(12) United States Patent
Cushner et al.

(10) Patent No.: US 9,907,454 B2
(45) Date of Patent: *Mar. 6, 2018

(54) GAS WATER BOTTLE ADAPTOR

(71) Applicant: UNITED STATES ENDOSCOPY GROUP, INC., Mentor, OH (US)

(72) Inventors: Jeffrey B. Cushner, Woodmere, NY (US); Kenneth E. Wolcott, Centerport, NY (US); Christopher R. Stebbins, Huntington Station, NY (US); James Burns, Purdys, NY (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,129

(22) Filed: May 8, 2015

(65) Prior Publication Data

US 2015/0238067 A1    Aug. 27, 2015

Related U.S. Application Data

(63) Continuation of application No. 14/301,747, filed on Jun. 11, 2014, now Pat. No. 9,049,984, which is a
(Continued)

(51) Int. Cl.
*A61B 1/00*        (2006.01)
*A61B 1/015*       (2006.01)
(Continued)

(52) U.S. Cl.
CPC ...... *A61B 1/00119* (2013.01); *A61B 1/00112* (2013.01); *A61B 1/00121* (2013.01);
(Continued)

(58) Field of Classification Search
CPC ............... A61M 39/20; A61B 17/3462; A61B 17/3464; A61B 17/3466; A61B 1/00112;
(Continued)

(56) References Cited

U.S. PATENT DOCUMENTS

| 1,034,170 A | 7/1912 | Vanier |
| 2,186,908 A | 1/1940 | Page et al. |

(Continued)

FOREIGN PATENT DOCUMENTS

| DE | 33 24 730 A1 | 1/1984 |
| EP | 0075153 | 3/1983 |

(Continued)

OTHER PUBLICATIONS

Office Action for U.S. Appl. No. 13/873,598, dated Nov. 16, 2015.
(Continued)

*Primary Examiner* — Ryan Henderson
(74) *Attorney, Agent, or Firm* — Calfee Halter & Griswold LLP

(57) ABSTRACT

The present invention provides a gas water bottle adaptor that is suitable for attachment to a water bottle and to a bottle cap. The adaptor can include a gas inlet on one side thereof suitable for attachment to the gas connection of an endoscope. A sealing member can be affixed to the adaptor to prevent leakage of any fluid (e.g., liquid or gas) that is inside of the water bottle. The adaptor may be used in endoscopy methods and is particularly useful for adding a secondary gas source to a water bottle.

14 Claims, 7 Drawing Sheets

Related U.S. Application Data continuation of application No. 12/424,211, filed on Apr. 15, 2009, now Pat. No. 8,790,244.

(60) Provisional application No. 61/124,238, filed on Apr. 16, 2008.

(51) Int. Cl.
  *A61B 1/12* (2006.01)
  *A61M 39/16* (2006.01)
  *A61M 39/10* (2006.01)

(52) U.S. Cl.
  CPC ...... *A61B 1/00128* (2013.01); *A61B 1/00137* (2013.01); *A61B 1/015* (2013.01); *A61B 1/12* (2013.01); *A61M 39/16* (2013.01); *A61M 2039/1077* (2013.01)

(58) Field of Classification Search
  CPC ............ A61B 1/00119; A61B 1/00121; A61B 1/00128; A61B 1/00137; A61B 1/015; A61B 1/12; A61B 1/126; A61B 1/127; A61B 1/128
  USPC ................ 600/132, 156–159; 604/317–326, 604/403–407
  See application file for complete search history.

(56) References Cited

U.S. PATENT DOCUMENTS

| | | |
|---|---|---|
| D189,383 S | 11/1960 | Macomber |
| 3,135,412 A | 6/1964 | Cornelius |
| 3,222,135 A | 12/1965 | Ashmead |
| 3,390,897 A | 7/1968 | Buell |
| D227,558 S | 7/1973 | Matthews, Jr. |
| 4,108,172 A | 8/1978 | Moore, Jr. |
| 4,258,721 A | 3/1981 | Parent et al. |
| 4,261,343 A | 4/1981 | Ouchi et al. |
| 4,261,345 A | 4/1981 | Yamaguchi |
| 4,262,671 A | 4/1981 | Kersten |
| 4,311,134 A | 1/1982 | Mitsui et al. |
| 4,325,362 A | 4/1982 | Ouchi et al. |
| 4,350,647 A * | 9/1982 | de la Cruz ........ A61M 16/0051 128/200.11 |
| D267,743 S | 1/1983 | Cummingham et al. |
| D271,618 S | 11/1983 | Nishigaki |
| 4,464,316 A | 8/1984 | Michaels |
| 4,474,574 A | 10/1984 | Wolfe et al. |
| 4,489,712 A | 12/1984 | Ohshima |
| 4,494,252 A | 1/1985 | Chaoui |
| 4,519,385 A | 5/1985 | Atkinson et al. |
| D280,206 S | 8/1985 | Ishii |
| 4,538,593 A | 9/1985 | Ishii |
| 4,539,586 A | 9/1985 | Danna et al. |
| 4,548,197 A | 10/1985 | Kinoshita |
| 4,550,716 A | 11/1985 | Kinoshita |
| 4,552,130 A | 11/1985 | Kinoshita |
| 4,637,378 A | 1/1987 | Sasa |
| 4,667,655 A | 5/1987 | Ogiu et al. |
| 4,691,701 A | 9/1987 | Williams |
| 4,701,159 A | 10/1987 | Brown et al. |
| 4,708,126 A | 11/1987 | Toda et al. |
| 4,748,970 A | 6/1988 | Nakajima |
| 4,760,838 A | 8/1988 | Fukuda |
| D299,538 S | 1/1989 | Balding et al. |
| 4,800,869 A | 1/1989 | Nakajima |
| 4,844,052 A | 7/1989 | Iwakoshi et al. |
| 4,857,062 A * | 8/1989 | Russell ............ A61M 39/0613 137/846 |
| 4,901,142 A | 2/1990 | Ikuno et al. |
| 4,905,852 A | 3/1990 | Zumbuhl |
| 4,968,309 A | 11/1990 | Andersson |
| 4,997,429 A | 3/1991 | Dickerhoff et al. |
| 5,027,791 A | 7/1991 | Takahashi |
| 5,054,481 A | 10/1991 | Shin |
| 5,083,549 A | 1/1992 | Cho et al. |
| 5,125,915 A | 6/1992 | Berry et al. |
| 5,133,336 A | 7/1992 | Savitt et al. |
| 5,163,576 A | 11/1992 | Galer |
| 5,176,629 A | 1/1993 | Kullas et al. |
| 5,192,439 A | 3/1993 | Roth et al. |
| 5,250,038 A * | 10/1993 | Melker ............ A61M 25/0032 604/167.01 |
| 5,254,083 A | 10/1993 | Gentelia |
| 5,297,537 A | 3/1994 | Savitt et al. |
| 5,309,906 A | 5/1994 | LaBombard |
| 5,333,603 A | 8/1994 | Schuman |
| 5,343,855 A | 9/1994 | Iida et al. |
| 5,381,924 A | 1/1995 | Kiefel |
| 5,402,770 A | 4/1995 | Iida et al. |
| 5,406,808 A | 4/1995 | Babb |
| 5,437,654 A | 8/1995 | McVay |
| 5,505,707 A | 4/1996 | Manzie et al. |
| 5,607,391 A | 3/1997 | Klinger et al. |
| 5,630,795 A | 5/1997 | Kuramoto et al. |
| 5,634,880 A | 6/1997 | Feldman et al. |
| 5,697,888 A | 12/1997 | Kobayashi et al. |
| D392,046 S | 3/1998 | Niedospial, Jr. |
| 5,755,360 A | 5/1998 | Elliott |
| 5,782,383 A | 7/1998 | Robinson |
| 5,810,718 A | 9/1998 | Akiba et al. |
| 5,810,770 A | 9/1998 | Chin |
| 5,830,128 A | 11/1998 | Tanaka |
| 5,902,264 A | 5/1999 | Toso et al. |
| 5,902,413 A | 5/1999 | Puszko et al. |
| 6,030,632 A | 2/2000 | Sawan |
| 6,189,870 B1 | 2/2001 | Withall |
| 6,210,322 B1 | 4/2001 | Byrne |
| 6,220,482 B1 | 4/2001 | Simmel et al. |
| 6,391,000 B1 | 5/2002 | Belikan et al. |
| 6,481,589 B2 | 11/2002 | Blomdahl et al. |
| 6,485,412 B1 | 11/2002 | Byrne |
| 6,485,684 B1 | 11/2002 | Mapson et al. |
| 6,558,317 B2 | 5/2003 | Takahashi et al. |
| 6,575,160 B1 | 6/2003 | Volgyesi |
| 6,575,946 B2 | 6/2003 | Sealfon |
| 6,702,738 B2 | 3/2004 | Ito |
| 6,764,442 B2 | 7/2004 | Ota et al. |
| 6,786,865 B2 | 9/2004 | Dhindsa |
| 6,837,400 B2 | 1/2005 | Leoncavallo et al. |
| 6,840,902 B2 | 1/2005 | Sano et al. |
| 6,855,109 B2 | 2/2005 | Obata et al. |
| 6,860,516 B2 | 3/2005 | Ouchi et al. |
| 6,881,188 B2 | 4/2005 | Furuya et al. |
| 6,984,204 B2 | 1/2006 | Akiba |
| 7,066,177 B2 | 6/2006 | Pittaway et al. |
| 7,297,121 B2 | 11/2007 | Turturro |
| 7,347,355 B2 | 3/2008 | Sato et al. |
| 7,399,273 B2 | 7/2008 | Moriyama et al. |
| 7,568,735 B2 | 8/2009 | Akiba |
| 7,578,294 B2 | 8/2009 | Pierro et al. |
| 7,582,056 B2 | 9/2009 | Noguchi et al. |
| 7,597,662 B2 | 10/2009 | Litscher et al. |
| D612,496 S | 3/2010 | Bennison |
| 7,678,044 B2 | 3/2010 | Fujikura |
| 7,766,898 B2 | 8/2010 | Mottola et al. |
| 7,806,850 B2 | 10/2010 | Williams, Jr. et al. |
| 7,824,329 B2 | 11/2010 | Aizenfeld et al. |
| 7,837,769 B2 | 11/2010 | Lahr |
| 7,892,223 B2 | 2/2011 | Geiselhart |
| 7,901,350 B2 | 3/2011 | Yamazaki |
| 7,914,519 B2 | 3/2011 | Moran et al. |
| D639,940 S | 6/2011 | Cushner et al. |
| 7,963,914 B2 | 6/2011 | Uchimura et al. |
| D652,923 S | 1/2012 | Kennedy et al. |
| 8,152,716 B2 | 4/2012 | Aizenfeld et al. |
| 8,343,041 B2 | 1/2013 | Byers et al. |
| 8,454,498 B2 | 6/2013 | Cushner et al. |
| 9,049,984 B2 | 6/2015 | Cushner et al. |
| 9,144,373 B2 | 9/2015 | Kaye et al. |
| 2002/0092858 A1 | 7/2002 | Bowman |
| 2003/0032860 A1 | 2/2003 | Avni et al. |
| 2003/0032862 A1 | 2/2003 | Ota et al. |

(56) References Cited

U.S. PATENT DOCUMENTS

| | | |
|---|---|---|
| 2003/0045779 A1 | 3/2003 | Ito |
| 2003/0073971 A1 | 4/2003 | Saker |
| 2003/0189023 A1 | 10/2003 | Gonzalez |
| 2004/0153047 A1 | 8/2004 | Blank et al. |
| 2004/0199052 A1 | 10/2004 | Banik et al. |
| 2004/0260151 A1 | 12/2004 | Akiba |
| 2005/0263480 A1 | 12/2005 | Smolko et al. |
| 2006/0052663 A1 | 3/2006 | Koitabashi |
| 2006/0052665 A1 | 3/2006 | Aizenfeld et al. |
| 2006/0068360 A1 | 3/2006 | Boulais |
| 2006/0106285 A1 | 5/2006 | Boulais et al. |
| 2006/0135851 A1 | 6/2006 | Yamazaki |
| 2006/0178648 A1 | 8/2006 | Barron et al. |
| 2006/0229498 A1 | 10/2006 | Kohno |
| 2006/0241348 A1 | 10/2006 | Kohno |
| 2006/0266423 A1 | 11/2006 | Akiba et al. |
| 2006/0276689 A1 | 12/2006 | Litscher et al. |
| 2006/0293562 A1 | 12/2006 | Uchimura et al. |
| 2007/0043261 A1 | 2/2007 | Watanabe et al. |
| 2007/0043262 A1 | 2/2007 | Levy et al. |
| 2007/0066866 A1 | 3/2007 | Noguchi et al. |
| 2007/0145738 A1 | 6/2007 | Akiba |
| 2007/0129705 A1 | 7/2007 | Trombley, III et al. |
| 2007/0225566 A1 | 9/2007 | Kawanishi |
| 2007/0238929 A1 | 10/2007 | Aizenfeld et al. |
| 2007/0244363 A1 | 10/2007 | Sano et al. |
| 2008/0072970 A1 | 3/2008 | Gasser et al. |
| 2008/0132763 A1 | 6/2008 | Isaacson |
| 2008/0154095 A1 | 6/2008 | Stubkjaer et al. |
| 2008/0214895 A1 | 9/2008 | Campos |
| 2008/0228258 A1* | 9/2008 | Gerdts ................ A61F 2/95 623/1.11 |
| 2008/0269560 A1 | 10/2008 | Ito et al. |
| 2008/0294123 A1* | 11/2008 | Lunn ................ A61B 17/3462 604/256 |
| 2009/0032533 A1 | 2/2009 | Kessell et al. |
| 2009/0101562 A1 | 4/2009 | Newton |
| 2009/0143719 A1 | 6/2009 | Loori et al. |
| 2009/0188919 A1 | 7/2009 | Takanohashi |
| 2009/0209822 A1 | 8/2009 | Ikeda |
| 2009/0260629 A1 | 10/2009 | Yee et al. |
| 2009/0264705 A1 | 10/2009 | Cushner et al. |
| 2009/0266357 A1 | 10/2009 | Varis et al. |
| 2009/0298129 A1 | 12/2009 | Spence et al. |
| 2010/0022834 A1 | 1/2010 | Noda et al. |
| 2010/0056867 A1 | 3/2010 | Labombard |
| 2010/0237070 A1 | 9/2010 | Coonce et al. |
| 2010/0292644 A1 | 11/2010 | Haack |
| 2011/0174822 A1 | 7/2011 | Gasser et al. |
| 2011/0263939 A1 | 10/2011 | Kaye et al. |
| 2011/0275945 A1 | 11/2011 | Karla et al. |
| 2012/0091092 A1 | 4/2012 | Adams |
| 2012/0209062 A1 | 8/2012 | Qiao |
| 2012/0277536 A1 | 11/2012 | Kaye |

FOREIGN PATENT DOCUMENTS

| | | | |
|---|---|---|---|
| EP | 0082950 A2 | 7/1983 | |
| EP | 0361086 A1 | 4/1990 | |
| EP | 0437229 A1 | 7/1991 | |
| EP | 2 428 157 A1 | 3/2012 | |
| JP | 62-125501 U | 8/1987 | |
| JP | 1099558 A | 4/1989 | |
| JP | H01280437 A | 11/1989 | |
| JP | 5168587 A | 7/1993 | |
| JP | 5220103 A | 8/1993 | |
| JP | 5337074 A | 12/1993 | |
| JP | 7-9301 | 2/1995 | |
| JP | 8106052 A | 4/1996 | |
| JP | 08112251 A | 5/1996 | |
| JP | 9164113 A | 6/1997 | |
| JP | 10099265 A | 4/1998 | |
| JP | 10-276963 A | 10/1998 | |
| JP | 2001299685 A | 10/2001 | |
| JP | 2002-177205 A | 6/2002 | |
| JP | 2003-024266 A | 1/2003 | |
| JP | 2003-070731 A | 3/2003 | |
| JP | 2003070731 A * | 3/2003 | ............... A61B 1/00 |
| JP | 2003111721 A | 4/2003 | |
| JP | 2003-339619 A | 12/2003 | |
| JP | 2004-147833 A | 5/2004 | |
| JP | 2004-242877 A | 9/2004 | |
| JP | 2004-305758 A | 11/2004 | |
| JP | 2005-021710 A | 1/2005 | |
| JP | 2005-245668 A | 9/2005 | |
| JP | 2005-304780 A | 11/2005 | |
| JP | 2006-042874 A | 2/2006 | |
| JP | 2006-110215 A | 4/2006 | |
| JP | 2006-116000 A | 5/2006 | |
| JP | 2006-167064 A | 6/2006 | |
| JP | 2006-280536 A | 10/2006 | |
| JP | 2007-089623 A | 4/2007 | |
| JP | 2007089623 A * | 4/2007 | ............... A61B 1/00 |
| JP | 2007-252834 A | 10/2007 | |
| JP | 2007-313047 A | 12/2007 | |
| JP | 2008-029742 A | 2/2008 | |
| JP | 2010-057728 A | 3/2010 | |
| WO | WO 93/14688 A1 | 8/1993 | |
| WO | 2004023987 | 3/2004 | |
| WO | WO 2006/109351 A1 | 10/2006 | |
| WO | WO-2008/122969 A1 | 10/2008 | |
| WO | WO 2009/129302 A1 | 10/2009 | |

OTHER PUBLICATIONS e-Scope (endoscope sales/services), e-Scope, LLC Brochure, dated Jan. 16, 2008, 2 pages.
Periphery Accesories Programme, Pentax Brochure, (undated), 20 pages.
Endoscope Channel Guide, Evis™ 40/140/240 & Exera™ 160-Series GI Endoscopes, Olympus America, Inc. (2003), 1 page.
International Preliminary Report on Patentability for Application No. PCT/US2010/046805 dated Mar. 15, 2012.
International Seaarch Report and Written Opinion for Applicaation No. PCT/US2010/046805 dated Dec. 7, 2010.
International Search Report and Written Opinion for International Application No. PCT/US2010/048578 dated Jan. 28, 2011.
International Search Report and Written Opinion for Application No. PCT/US2009/040655 dated Jul. 9, 2009.
International Preliminary Report on Patentability for Application No. PCT/US2009/040655 dated Oct. 19, 2010.
International Search Report for Application No. PCT/US2014/025948 dated Jul. 29, 2014.
International Search Report and Written Opinion for Application No. PCT/US2013/032005 dated Jun. 18, 2013.
Office Action for Canadian Application No. 2,772,341 dated Nov. 3, 2014.
Office Action for Chinese Application No. 201080046225.0 dated May 4, 2014.
Office Action for Chinese Application No. 200980113305.0 dated Nov. 16, 2011.
Notice of Decision of Granting Patent for Chinese Application No. 200980113305.0 dated Apr. 9, 2012.
Communication Pursuant to Article 94(3) EPC for Application No. 10 749 572.3; dated Nov. 29, 2013.
Communication for European Patent Application No. 09 731 691.3, dated Dec. 5, 2011, 4 pages.
Office Action for European Application No. 09 731 691.3 dated Oct. 28, 2014.
Office Action for Japanese Application No. 2012-526984; dated May 31, 2013.
Office Action for Japanese Patent Application No. 2011-505165 dated Sep. 21, 2012.
Office Action for U.S. Appl. No. 29/335,421 dated Dec. 7, 2010.
Notice of Allowance for Design U.S. Appl. No. 29/335,421 dated Feb. 10, 2011.
Office Action for U.S. Appl. No. 12/424,211 dated Apr. 23, 2012.
Office Action for U.S. Appl. No. 12/424,211 dated Oct. 5, 2012.

(56) References Cited

OTHER PUBLICATIONS

Office Action for U.S. Appl. No. 12/424,211 dated Dec. 4, 2013.
Notice of Allowance for U.S. Appl. No. 12/424,211 dated Mar. 28, 2014.
U.S. Appl. No. 12/869,265, filed Aug. 26, 2010; In re: Cushner et. al.; entitled *In-Line Gas Adaptor for Endoseopie Apparatus*.
Office Action for U.S. Appl. No. 12/869,265 dated Aug. 16, 2012.
Notice of Allowance for U.S. Appl. No. 12/869,265 dated Feb. 4, 2013.
Office Action for U.S. Appl. No. 12/881,683 dated Aug. 22, 2012.
Notice of Allowance for U.S. Appl. No. 12/881,683 dated Feb. 7, 2013.
Office Action for U.S. Appl. No. 13/873,598 dated Mar. 26, 2015.
Office Action for U.S. Appl. No. 13/874,568 dated Mar. 26, 2015.
Notice of Allowance for U.S. Appl. No. 14/301,747 dated Mar. 31, 2015.
Office Action for U.S. Appl. No. 13/873,598 dated Jul. 30, 2015.
Office Action for U.S. Appl. No. 13/874,568 dated Jul. 30, 2015.
Notice of Allowance from U.S. Appl. No. 12/881,683 dated Apr. 12, 2013.
Office Action from U.S. Appl. No. 13/464,263 dated Mar. 11, 2014.
Office Action from U.S. Appl. No. 13/093,989 dated Nov. 10, 2014.
Notice of Allowance from U.S. Appl. No. 13/093,989 dated May 27, 2015.
Office Action from U.S. Appl. No. 14/387,309 dated May 18, 2016.
Office Action from U.S. Appl. No. 14/456,783 dated Mar. 19, 2015.
Response to Office action from U.S. Appl. No. 14/456,783 dated Aug. 19, 2015.
Office Action from U.S. Appl. No. 14/456,783 dated Sep. 10, 2015.
Response to Office Action from U.S. Appl. No. 14/456,783 dated Jan. 11, 2016.
Office Action from U.S. Appl. No. 14/456,783 dated Mar. 10, 2016.
Weng et al., "Fundamentals and Material Development for Thermoplastic Elastomer (TPE) Overmolding", in Journal of Injection Molding Technology, vol. 4, No. 1, Mar. 2000.
Amendment from U.S. Appl. No. 14/387,309 dated Feb. 15, 2017.
Office Action from U.S. Appl. No. 14/387,309 dated Mar. 21, 2017.
Response to Office Action from U.S. Appl. No. 14/456,783 dated Sep. 8, 2016.
Office Action from U.S. Appl. No. 14/456,783 dated Sep. 29, 2016.
Amendment from U.S. Appl. No. 14/387,309 dated Sep. 1, 2016.
Final Office Action from U.S. Appl. No. 14/387,309 dated Oct. 11, 2016.
Office Action from European Application No. 09731691.3 dated Oct. 7, 2016.
Response to Office Action from U.S. Appl. No. 14/456,783 dated Dec. 29, 2016.
Office Action from U.S. Appl. No. 14/456,783 dated Jan. 13, 2017.
Response to Office Action from U.S. Appl. No. 14/456,783 dated May 11, 2017.
Notice of Non-Compliant Amendment from U.S. Appl. No. 14/456,783 dated May 18, 2017.
Response to Notice of Non-Compliant Amendment from U.S. Appl. No. 14/456,783 dated May 18, 2017.
Office Action from U.S. Appl. No. 14/456,783 dated Jun. 7, 2017.
Response to Office Action U.S. Appl. No. 14/387,309 dated Jun. 21, 2017.
Office Action from U.S. Appl. No. 14/387,309 dated Aug. 4, 2017.

\* cited by examiner

GAS WATER BOTTLE ADAPTOR

CROSS-REFERENCE TO RELATED APPLICATIONS

The present application is a continuation of U.S. patent application Ser. No. 14/301,747, filed Jun. 11, 2014, which is a continuation of U.S. patent application Ser. No. 12/424,211, filed Apr. 15, 2009 (now U.S. Pat. No. 8,790,244), which claims priority to U.S. Provisional Patent Application No. 61/124,238, filed Apr. 16, 2008, the content of each of which is incorporated herein by reference in its entirety.

FIELD OF THE INVENTION

The present application is directed to devices used in surgical procedures, such as endoscopic procedures, and more particularly to a device that can be used to add a secondary gas source to a water bottle, such as for use in endoscopy.

BACKGROUND

Many invasive medical procedures that previously required major surgery are now performed using endoscopic instruments. Such instruments can provide an internal view of particular body parts, organs, or passages without requiring invasive surgery.

Generally, an endoscopic instrument may include one or more channels through which miniaturized, flexible instruments can be inserted and advanced. The endoscope typically includes an elongated flexible cable equipped at one end with an eyepiece or other viewing means and at the other end with an optical head. Only the head is directly and externally connected to the instrument. The cable transmits images or image-producing signals from the illuminated operative site to the viewing means to provide the instrument operator with full vision of the actions being performed at the instrument's working end. A coherent optic bundle extends from the head and through the flexible cable through the eyepiece for providing the surgeon with visual confirmation of the instrument's tip or jaw action. The illuminating means may take the form a light-transmitting waveguide extending through the cable to illuminate the operative area. The waveguide is connected at its proximal end to a suitable high-intensity light source.

The cable of an endoscope also provides a flow passage for the delivery of fluid (e.g., liquid or gas) for irrigation or other purposes. Typically, the flow passage and the illuminating means are disposed on opposite sides of the coherent image-transmitting waveguide. In conventional practice, it is necessary to provide a flow of sterile water across the optic head to prevent the buildup of materials (e.g., surgical debris and body fluids) on the optic head. This flow of water operates, in a sense, like a windshield wiper/washer assembly.

In common designs, an endoscopic instrument typically has a control body which is connected by a light guide tube to a light guide connector, which actually can include a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body.

Alternatively, the control body can also include a water port so as to allow water to be directly provided to the control body. Suitable valves are provided on the control body so as to control the flow of water through the control body and over the optic head of the instrument.

For example, FIG. 1 illustrates an endoscope system that is unmodified (i.e., includes no secondary gas supply means). The endoscope is shown to include a shaft (insertion tube) connected to a control body that includes a biopsy port, air-water and suction valves, and angulation controls. The control body is connected to an umbilical (light guide connecting tube) that further connects to an electrical pin unit, which is directly connected to a light source and is connected via a video connection lead (and plug) to a video processor. The image produced by the endoscope is transmitted via a fiber optic bundle, or electronically from a charge-coupled device (CCD) chip. FIG. 1 illustrates a video monitor and attached keyboard for viewing images and inputting commands. The electrical pin unit includes a port for a water bottle connector that connects to a water bottle for providing irrigation.

The somewhat complex internal anatomy of the endoscope is further illustrated in FIG. 2, which shows a detailed view of the endoscope from FIG. 1. As seen in FIG. 2, the shaft incorporates an instrumentation channel extending from the entry biopsy port to the tip of the instrument. Channel sizes can vary from about 1 to 5 mm. Again, the endoscope includes no means for a secondary gas supply.

Unexpectedly, there is usually a great expense associated with the delivery of sterile water in an endoscopy system. As seen in FIG. 1, the known practice has been to use a water bottle with a cap having a tube running therethrough. The tube typically has a fitting at the end distal to the bottle to allow for connection to the air/water connection port of the light guide connector (of the electrical pin unit, as illustrated in FIG. 1) or to the port on the endoscope control body. Typically, the tube connecting the water bottle to the endoscope is formed of an inner tube and an outer tube. The outer tube extends into the water bottle and is connected to the cap of the water bottle. In normal practice, air is delivered through the area between the inner tube and the outer tube so as to pressurize the interior of the water bottle and force water to flow through the tube and into the endoscope at a desired rate.

The known water bottle configuration presents several problems. First is the issue of cost and sterilization. For example, the guide accompanying one known endoscope device includes the following instructions:

Failure to properly clean and high-level disinfect endoscopic equipment after each examination can compromise patient safety.

Every channel of the endoscope must be reprocessed each time the endoscope is used, even if the channel was not utilized during the preceding patient procedure.

Every channel must go through every reprocessing step (cleaning, disinfection, rinsing, alcohol-air drying).

In practice, after usage, the water bottle, its associated tubing, and its associated fittings are sterilized, such as by glutaraldehyde disinfection and/or autoclaving. This creates a considerable expense to the hospital including the considerable labor expense associated with the disinfection of the water bottle. There is also the possibility of residual contaminants residing in the area of connection between the tubes and the bottle. It also has not typically been feasible to simply dispose of a water bottle after a single use because of the expense associated with the water bottle/cap/tubing systems.

Another issue with known water bottles is the gas source. Ambient air is often pumped into the system to charge the water bottle, as described above. It can be desirable, however, to use a secondary gas source instead of ambient air. Known devices allowing for substitution with a secondary gas source are excessively expensive and can still suffer the problems associated with disinfection after each use. The present invention beneficially provides a solution to these and other problems associated with known water bottles for use in endoscopy systems.

SUMMARY OF THE INVENTION

The present invention provides adaptors to improve and extend the use of water bottles in endoscopy. The adaptors make it possible to use a variety of standard bottles with a variety of standard bottle caps. Since endoscopy equipment must either be thoroughly disinfected between uses, or otherwise discarded, the inventive adaptor beneficially makes it possible to more economical bottles and/or reduce the time spent cleaning equipment. The adaptors also provide for the use of a secondary gas in an endoscopy procedure without the requirement of a costly, specialized bottle and/or cap. Rather, the inventive adaptor effectively makes any combination of water bottle and cap a gas-ready water bottle system. These and other benefits of the present invention are more fully described herein.

In certain embodiments, the present invention is directed to an adaptor for adding a secondary gas source to an endoscopic water bottle. Specifically, the adaptor may comprise a substantially tubular body having an interior surface and an exterior surface and having an upper portion and a lower portion, which particularly may be characterized as being flared. The upper body portion preferably can have threads on the exterior surface thereof making the upper body portion suitable for attachment to threads on a water bottle cap. The lower body portion similarly can have threads on the interior surface thereof making it suitable for attachment to threads on a neck portion of the water bottle. The adaptor further can comprise a gas inlet port. Such port particularly may extend outward from the exterior surface of the body. The port specifically can have a central passage that extends through the adaptor body and opens on the interior surface of the adaptor body.

In other embodiments, the adaptor of the invention also may comprise one or more sealing members. Such member may be associated with the exterior surface of the upper body portion, such as for forming a fluid tight seal between the adaptor and the water bottle cap. Such member further may be associated with the interior surface of the lower body portion, such as for forming a fluid tight seal between the adaptor and the water bottle. An O-ring is one non-limiting example of sealing members that may be used according to the invention.

In particular embodiments, the adaptor may include specific structures to accommodate the sealing members. For example, the adaptor further may comprise a groove formed in the exterior surface near the top of the upper body portion for receiving the sealing member. Similar structure could be included in relation to a sealing member associated with the interior surface of the lower body portion.

In other embodiments, the adaptor also may comprise a component for closing the gas inlet port to fluid passage. For example, in one embodiment, the adaptor further may comprise a cap, although other closure means are also envisioned.

The gas inlet port itself also may take on a specific structure. For example, in some embodiments, the gas inlet port can comprise a luer connector. Other types of connectors, such as Swagelok fittings or quick-connect fittings may be used, the only limitation being that the gas inlet port is preferably a connector that would be suitable for attachment of a gas line.

The interconnection of the gas inlet port and the adaptor main body can vary according to different embodiments of the invention. For example, the adaptor body and the gas inlet port can be distinct parts that are connected together by some means (preferably to form a fluid-tight connection). Still further, it is possible for the adaptor body itself to be formed of multiple distinct components. For example, the upper body portion and the lower body portion may be separately formed and then combined by some suitable means. In other embodiments, however, the adaptor body and gas inlet port can be a single, monolithic structure.

The adaptor of the invention can be a machined part, can be a molded part, or can be a part formed by any other suitable means for forming a structure as described herein. Moreover, the adaptor can be a single-use component (i.e., disposable) or can be reusable (i.e., can be cleaned and disinfected one or more times to allow for multiple uses). The adaptor also can be formed from a variety of materials, such as metal materials or polymeric materials.

The invention further can comprise a complete water bottle assembly for use with an endoscope. In specific embodiments, the assembly may comprise a water bottle, a water bottle cap, and an adaptor according to the present invention.

In other embodiments, the invention can be directed to a variety of methods. For example, the invention can encompass a method of performing an endoscopic procedure. Such a method can comprise using an endoscope assembly including a water bottle with a cap and also using an adaptor according to the invention. Such a method also could be carried out using a complete water bottle assembly, as described herein, that includes the inventive adaptor.

In still further embodiments, the invention can be directed to methods for supplying a secondary gas in an endoscopic procedure. For example, in one embodiment, the method can comprise using an endoscopy assembly having attached thereto a water bottle with a cap, affixing between the water bottle and the cap an adaptor according to the invention, and supplying a secondary gas to the endoscopy assembly via the adaptor. One example of a secondary gas that may be supplied according to this embodiment of the invention is carbon dioxide.

BRIEF DESCRIPTION OF THE DRAWINGS

Figure 1:
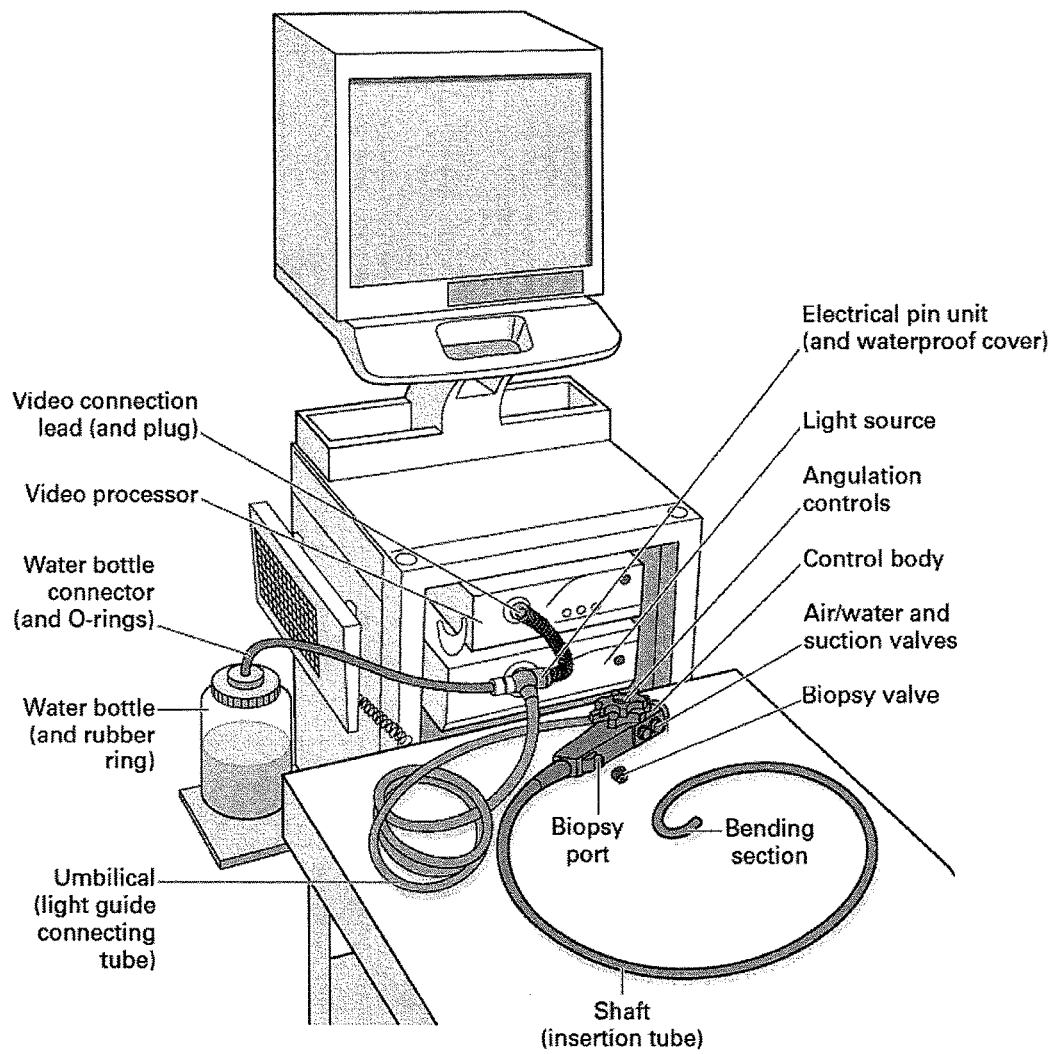
Figure 2:
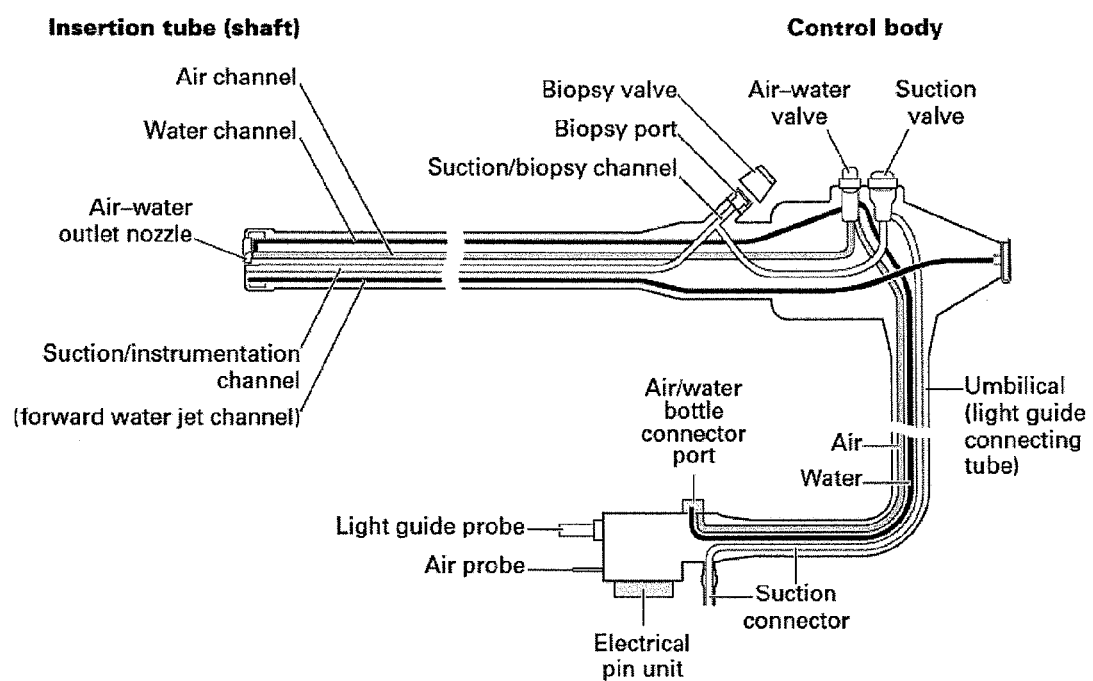
Figure 3:
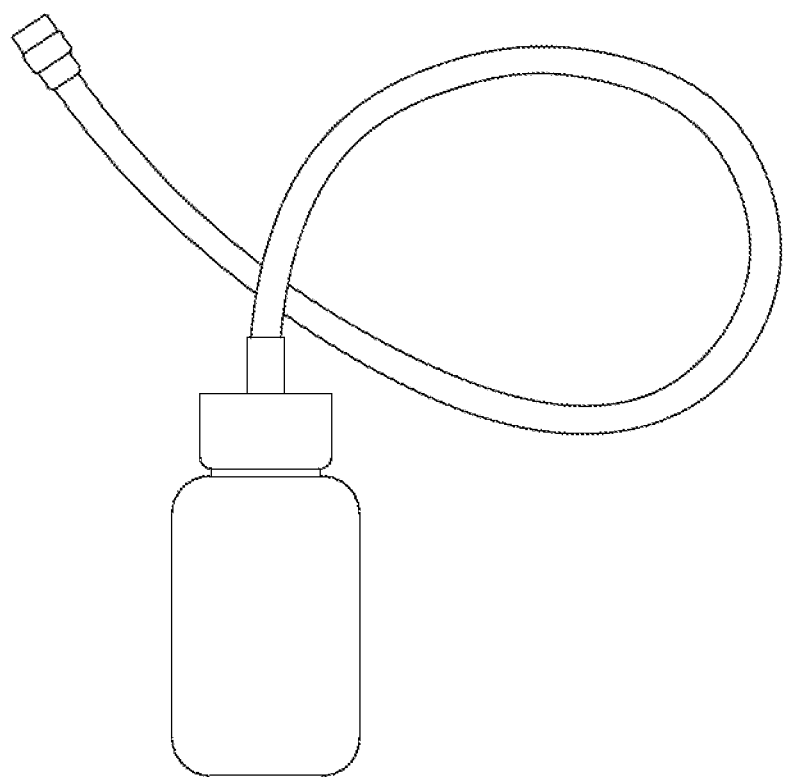
Figure 4:
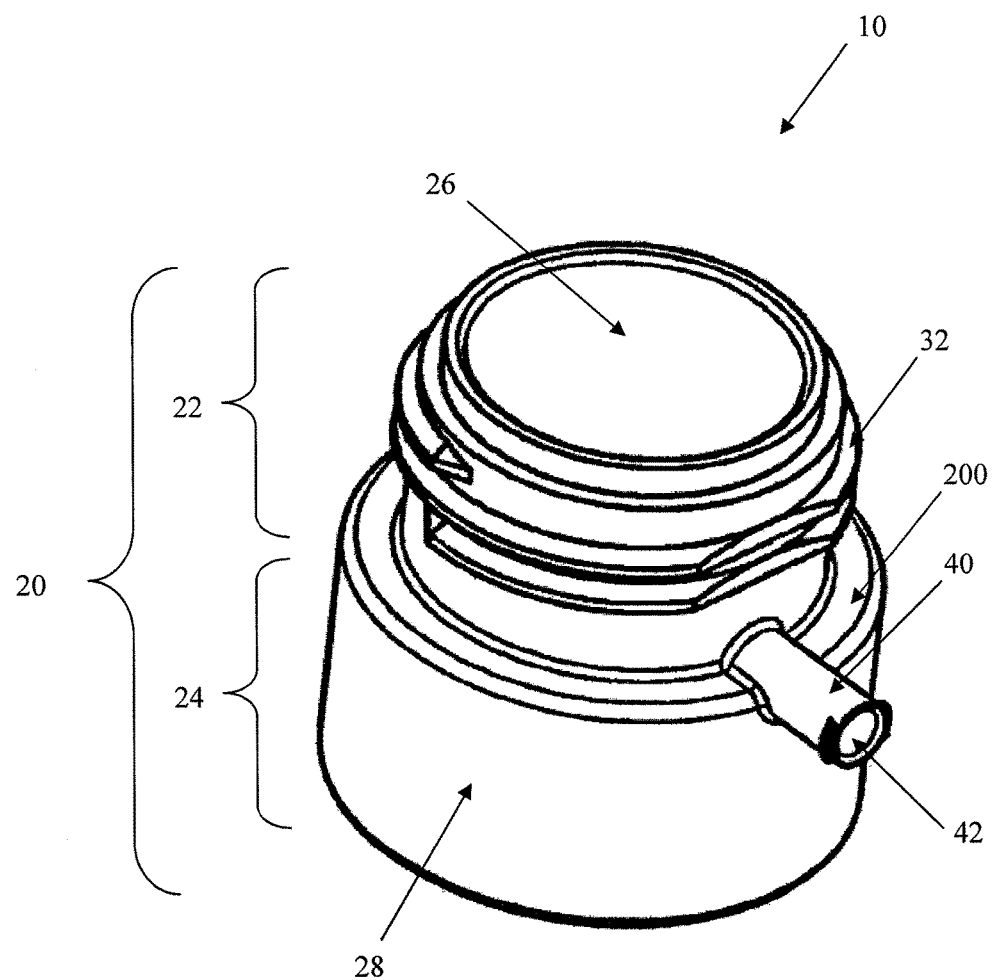
Figure 5:
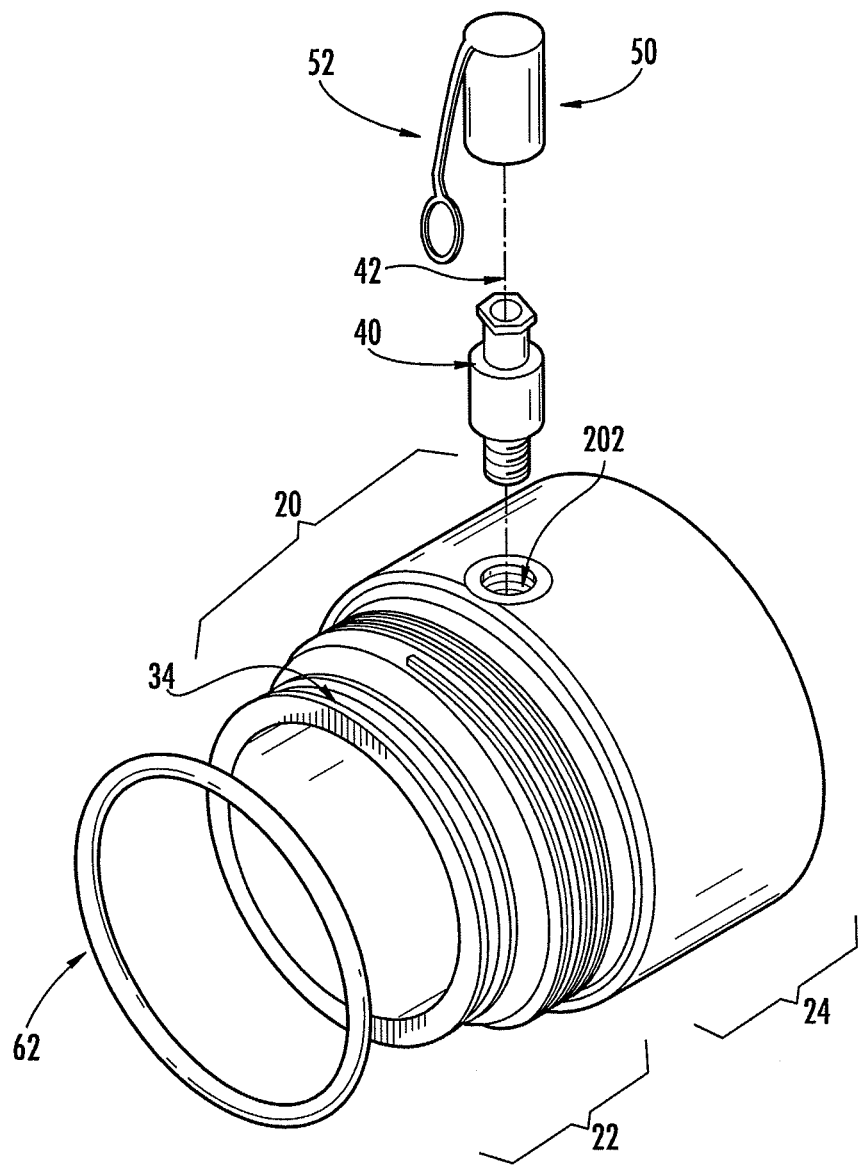
Figure 6:
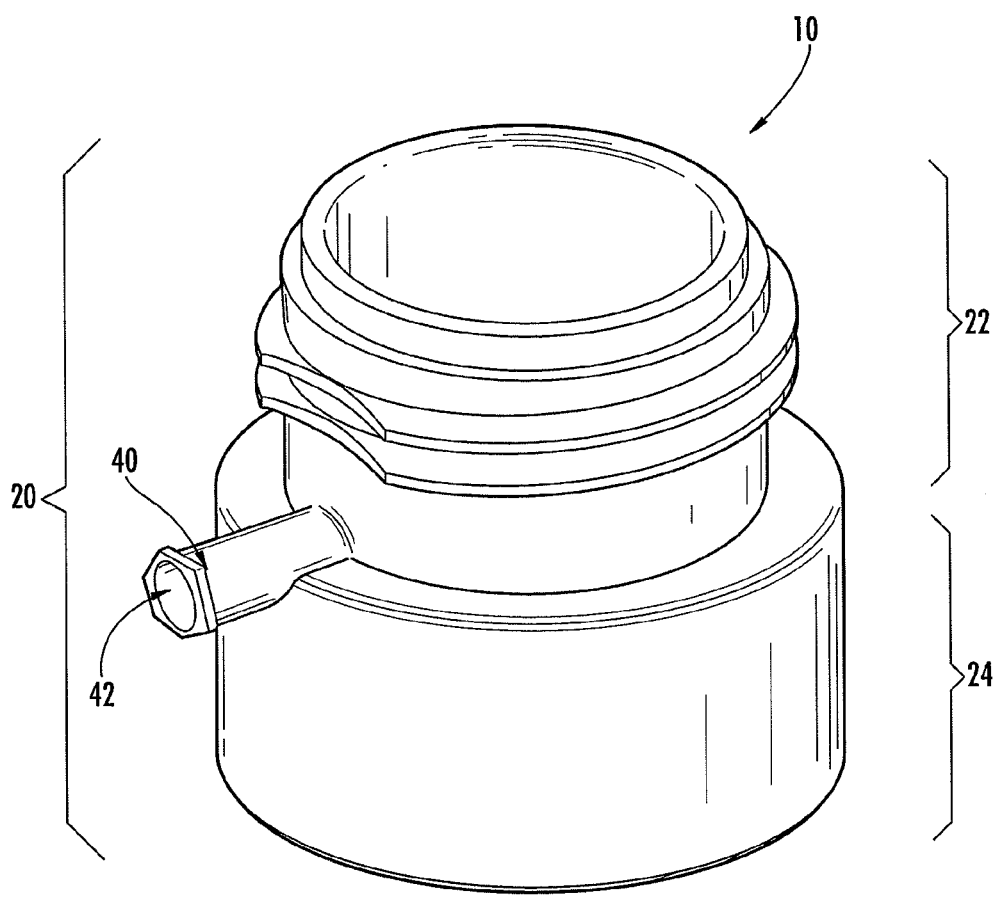
Figure 7:
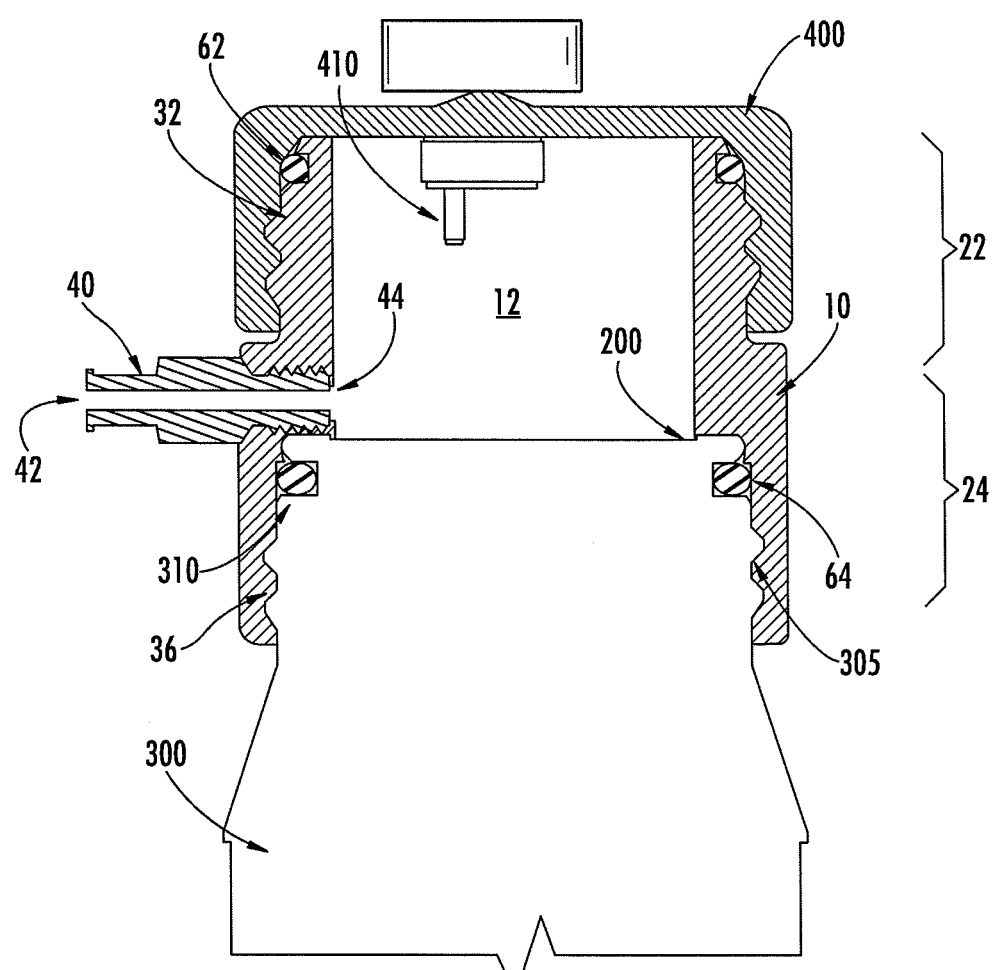

Having thus described the invention in general terms, reference will now be made to the accompanying drawing, which is not necessarily drawn to scale, and wherein:

FIG. 1 is an illustration of an unmodified endoscope system that includes no means of providing a secondary gas supply;

FIG. 2 is a detailed view of the endoscope from the system illustrated in FIG. 1;

FIG. 3 is an illustration of a water bottle for use with an endoscope system and that includes a cap with a water delivery tube but does not include means for providing a secondary gas supply;

FIG. 4 is a perspective view of an adaptor according to one embodiment of the invention;

FIG. 5 is an exploded view of an adaptor according to one embodiment of the invention;

FIG. 6 is a perspective view of an adaptor according to another embodiment of the invention; and FIG. 7 is a partial vertical cross-section of an adaptor according to one embodiment of the invention having a water bottle affixed to the lower portion of the adaptor and having a cap affixed to the upper portion of the adaptor.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides an adaptor that allows for the use of any secondary gas during an endoscopic procedure. As described previously, typical water bottle caps include a dual-lumen tube that supplies air through one lumen to charge the water bottle. Any gas provided during an endoscopic procedure in addition to or in lieu of this charge gas may be considered to be a secondary gas according to the present invention. The ability to use any secondary gas of choice according to the invention can be achieved through provision of an adaptor for use with an endoscopy water bottle and cap. The adaptor has the added advantage of at least partially eliminating the costs associated with continually replacing expensive single-use bottle/cap systems and/or continually disinfecting reusable bottle/cap systems.

In reality, medical and veterinary institutions and professionals typically have a number of inexpensive bottles that could be used with an endoscopic system. The adaptor of the present invention does away with the need to use specialized water bottles that may cost several hundred dollars apiece. The present invention also does away with the need for highly specialized water bottle caps. In an effort to allow for the use of a secondary gas, one option has been a highly specialized bottle cap that includes a typical dual-lumen tube, as described in relation to the known art, but also including a second tube attached to the cap to provide addition of a secondary gas. Such a device is disadvantageous, however, because it is designed for one-time use only and cannot be reprocessed according to known disinfecting procedures. Still further, such device also carries a substantially high cost per part that effectively cancels out any cost savings in relation to the ability to use the device with cheaper bottles. The present invention, on the contrary, provides at least the same advantages of this known device without being hindered by the noted disadvantages.

In one aspect, the present invention thus provides an adaptor for converting an endoscopic water bottle into a gas ready bottle. The invention is particularly beneficial in that the adaptor can be used with a wide variety of single use or reusable water bottles. Generally, water bottles for use in endoscopy are of a somewhat standard size in relation to bottle volume, bottle neck diameter, and threads present. For example, FIG. 3 illustrates a water bottle and cap with tube extending therefrom. Thus, the adaptor of the invention can be made to have somewhat standardized dimension to accommodate standard bottle neck sizes. In one embodiment, the adaptor may be sized to fit one standard water bottle neck size and, in another embodiment, the adaptor may be sized to fit a different standard water bottle neck size. The invention thus encompasses a number of different embodiments of the water bottle adaptor that may vary only in the sizing of certain components of the adaptor. Of course, different embodiments of the invention may differ in other aspects as well, as further described herein.

One embodiment of an adaptor 10 according to the present invention is illustrated in FIG. 4. As seen therein, the adaptor 10 can comprise a main body 20 that is preferably substantially tubular in structure. The body 20 can be characterized has having an upper portion 22 and a lower portion 24. Such characterization can be descriptive of the nature of forming the adaptor in that it can be two physically separate parts that are combined to form a single device. Such mode of combination can be by any means useful for combining parts depending upon the type of material from which the parts are constructed. For example, combining may be via welding, gluing, or any other means suitable in the art.

In certain embodiments, characterization of the upper portion 22 and lower portion 24 can be merely to allow for full description of the overall structure herein and may not be indicative of the method of forming the adaptor 10. In such embodiments, the body 20 of the adaptor 10 may be a single, monolithic structure (e.g., having a seamless construction).

The body 20 adaptor 10 of the invention also may be described has having an interior surface 26 and an exterior surface 28. These surfaces can be substantially smooth or may have a variety of different textures applied thereto or formed therein. These surfaces also may provide an area for placement of components useful for affixing the adaptor 10 to other components, such as a water bottle and/or a bottle cap. In particular, the further components may be threads. FIG. 4 illustrates threads 32 on the upper portion 22 of the main body 20. Although not illustrated in FIG. 4, in further embodiments, the lower portion 24 of the body 20 may also include threads, which may be of the same structure as the threads included on the upper portion 22 or may be of a different structure. In preferred embodiments, the lower portion 24 includes threads on the interior surface thereof.

In one embodiment, the threads 32 on the exterior surface of the upper portion 22 of the main body 20 are suitable for attachment to threads on a water bottle cap. In another embodiment, the threads on the interior surface of the lower portion 24 of the main body 20 are suitable for attachment to threads on a neck portion of a water bottle. In this sense, the words attach and affix, when used in relation to a threaded attachment, are intended to mean a releasable arrangement wherein the various components can be attached or affixed together by a screwing motion utilizing the threads and also may be detached by unscrewing.

The adaptor 20 may be a straight convertor in that the cap that is suitable to attach to the threads of the upper portion 22 would also attach to the threads of the neck of a water bottle that would be suitable to attach to the threads of the lower portion 24 of the main body 20. In other embodiments, the adaptor 20 may be a step-up or a step-down convertor. By this is meant that the cap that is suitable to attach to the threads of the upper portion 22 may be larger or smaller than a cap that would attach to the threads of the neck of a water bottle that would be suitable to attach to the threads of the lower portion 24 of the main body 20. The term "step-up" may be used in relation to attaching a cap that is larger than a cap designed to fit the water bottle being attached to the adaptor. The term "step-down" may be used in relation to attaching a cap that is smaller than a cap designed to fit the water bottle being attached to the adaptor.

The upper portion 22 and the lower portion 24 of the main body 20 may be structurally distinguished by the relative sizes of the separate portions. In particular, one of the upper and lower portions may have an outside diameter that is greater than the outside diameter of the other. In one embodiment, the lower portion 24 particularly can have a greater outside diameter than the upper portion 22. Thus, the lower portion 24 may be described as being flared. In relation to this structural nature, the lower portion 24 may further may be described as having a substantially horizontal ledge 200, which may be present on one or both of the interior surface 26 and the exterior surface 28. Such horizontal ledge 200 may be relevant to further structure and/or function of the adaptor 10, as further described below.

In further embodiments, the relation of the upper portion 22 to the lower portion 24 of the main body 24 may be described in terms of an interior diameter of the two portions. For example, in some embodiments, the interior diameter of the upper body portion 22 can be less than the interior diameter of the lower body portion 24. The transition of the different interior dimensions can be gradual or can be distinct. For example, a substantially horizontal ledge (as described above) may be formed on the interior surface of the main body 20 at the point where the interior diameter increases moving from the upper portion 22 to the lower portion 24.

In specific embodiments, the adaptor 20 further comprises a gas inlet port 40. This component of the adaptor 20 may take on a variety of structures and can have any structure or take on any form suitable to carry out the intended function, which is to provide a port for inputting a secondary gas into the device. In practice, a secondary gas often may be provided via some type of tubing that may or may not include a specialized connection unit (e.g., a screw-on connection or a plug-in connection). Thus, the gas inlet port 40 may be designed to accommodate such a specialized connection. Regardless of the type of connection that is to be accommodated, the gas inlet port 40 can comprise a central passage 42 extending through the main body 20 and opening on the interior surface of the main body 20. Such central passage 42 can be solely for passage of the secondary gas or also can form an entry port for insertion of a gas connection. For example, if the gas is to be provided via a device having a specialized plug-in connector, the passage 42 can be formed to accommodate the plug. Thus, the passage 42 can be described as being an annular passage with walls that may have formed therein specialized components (e.g., grooves or threads) for receiving a plug. The components particularly may allow for removable attachment of a plug device for delivery of gas.

In specific embodiments, the gas inlet port 40 may substantially extend outward from the exterior surface 28 of the main body 20. Such a structure particularly is useful to accommodate attachment of a gas line having a screw-on component or a gas line that attaches by simply being pressed over and onto the extending portion of the port 40 (e.g., a standard, flexible hose or tube).

In one embodiment, the gas inlet port 40 may comprise a luer connector or any similar structure. Luer connection systems typically are associated with the interconnection of syringes, catheters, hubbed needles, IV tubes, and the like. A luer connection system consists of round male and female interlocking tubes that may be slightly tapered to hold together better with even just a simple pressure/twist fit. As illustrated in FIG. 4, the luer connector is a female component. In use, a male luer connector may simply slip inside the shown female component and form a secure connection. The illustrated embodiment provides for an even more secure fit through inclusion of an additional outer rim (which functions as a single thread). In use, the male luer connector can include an additional outer rim of threading to form a "locked" connection.

In other embodiments, the adaptor 20 also may comprise a component for closing the gas inlet port 40 to fluid passage. Such component simply may comprise a sealing rod or other similar structure that may be inserted into the passage 42. As illustrated in FIG. 5, the component may comprise a cap 50, which can be formed of any material useful for covering the port 40. Preferably, the cap 50 is useful to form a fluid-tight seal on the gas inlet port. By fluid-tight is meant at least water-tight and, preferably, water-tight and gastight. In specific embodiments, the cap 50 may include a tether 52 for attaching the cap 50 to the adapter 20 to prevent loss of the cap 50 when not in use.

As seen in FIG. 5, the gas inlet port 40 may be a unitary structure or component that is (at least during construction) separate from the main body 20. Thus, the adaptor 10 may be described as comprising a first monolithic structure (i.e., the main body 20) having a passage 202 formed therein and a second structure (i.e., the gas inlet port 40) that can be inserted into the passage 202 formed in the adaptor body 20. As illustrated in FIG. 5, the gas inlet port 40 includes a threaded portion that is attached to the main body 20 via screwing into complimentary threads formed in the passage 202 formed in the main body 20. The invention also encompasses other methods of attaching a separate gas inlet port to the main body said attachment being detachable (such as a press fit, with or without an accompanying gasket component) or permanent (such as gluing or welding).

In another embodiment, as more particularly illustrated in FIG. 6, the adaptor body 20 and the gas inlet port 40 can be a single, monolithic structure. In other words, the adapter is not formed such that the gas inlet port 40 is inserted into the body 20 after formation of the respective, separate components. Rather, the gas inlet port 40 is monolithically formed with the main body 20 such that the gas inlet port 40 cannot be separated from the main body 20 without destructive means. This is evident in FIG. 6 by the seamless transition from the gas inlet port 40 to the main body 20. FIG. 6 again illustrates the gas inlet port 20 to be formed as a luer connector.

The adaptor of the invention also may comprise further components. For example, the adapter may comprise one or more sealing members. The sealing members may comprise any structure recognized as useful for providing a fluid-tight connection between two removably affixed parts (such as a water bottle cap and the inventive adaptor). Gaskets, O-rings, and other similar structures may be used. As shown in FIG. 5, the sealing member may be an O-ring. As further seen therein, the sealing member 62 may be associated with the exterior surface of the upper body portion 22 for forming a fluid tight seal between the adaptor 10 and a water bottle cap. The sealing member may fit flat against the top surface of the adaptor 10. In other embodiments, the upper body portion 22 may comprise a groove 34 formed in the exterior surface (preferably near the top) for receiving the sealing member 62. In use, the O-ring would be stretched over the top of the adaptor and seated in the groove. Preferably, the groove is formed above the threads of the upper body portion.

The adaptor also may comprise a sealing member associated with the interior surface of the lower body portion, which may be useful for forming a fluid tight seal between the adaptor and a water bottle. This particularly is illustrated in FIG. 7, which provides a cross-section that further illustrates the interaction between the adaptor 10, a water bottle 300, and a cap 400. In this embodiment, the water bottle 300 includes a groove 310 formed near the top of the neck 305, and a sealing member 64 (in this embodiment, an O-ring) is seated in the groove 310. The cap 400 is affixed to the adaptor 10 via the threads 32 on the adaptor 10, and the adaptor 10 is affixed to the bottle 300 via the threads 36 on the adaptor 10. Of course, it is understood that there are corresponding threads on the cap and the bottle to interact with the noted threads on the adaptor.

The illustration of FIG. 7 also makes visible further components of the inventive adaptor 10. For example, it is possible to see the substantially horizontal ledge 200 formed on the interior surface of the body 20. As seen, this ledge particularly can delineate the interior surface of the upper body portion 22 from the interior surface of the lower body portion 24. Further, the ledge 200 can provide a substantially flat surface against which the top surface of the water bottle neck portions seats.

As further seen in FIG. 7, the adaptor 10 provides an open interior passage 12 between the water bottle 300 affixed to the lower body portion 24 and the water bottle cap 400 affixed to the upper body portion 22. This open interior passage 12 allows a standard tube to be connected to the water bottle cap 400, such as by attachment to connector 410, and to freely extend into the water bottle 300.

In specific embodiments, the gas inlet port 40 can be positioned such that the opening 44 on the interior surface of the body 20 is located substantially between the threads 32 on the upper body portion 22 and the threads 36 on the lower body portion 24. This beneficially prevents the bottle cap or the bottle itself from interfering with exterior access to the gas inlet port or preventing input gas from entering the interior of the apparatus.

As noted above, the adaptor of the invention can be formed of a variety of different materials, which may affect how the adaptor is formed. In certain embodiments, the adaptor may be a machined part. As such, the adaptor particularly may comprise a plurality of individual parts that are machined separately and then combined to form the final adaptor assembly. Such combination can be by any means recognized as useful in the art, such as welding or using further attachment components, such as bolts, screws, rivets, or the like. In other embodiments, the individual parts may be threaded so they can be screwed together to form the final adaptor assembly. Such means is illustrated in FIG. 5 in relation to combining the gas inlet port 40 with the main body 20 which, in the embodiment of FIG. 5 is itself a single, monolithic structure but could be formed of a plurality of parts.

In other embodiments, the inventive adaptor may be a molded part. This particularly is advantageous for providing the adaptor as a single, monolithic structure. For example, as shown in FIG. 6, the main body 20 and the gas inlet port 40 are formed as a single, monolithic structure, which provides for a seamless construction. In embodiments where the adaptor is reusable, this simplifies cleaning and ensures no contaminants remain in seams, etc., existing between multiple parts that may be combined to form the adaptor. Moreover, any sealing members that are associated with the adaptor may be removed for cleaning purposes and may be disposable so that the adaptor itself can be reused with a new, sterile sealing member.

The adaptor of the invention is also beneficial in that it can be provided as a single-use adaptor or may be provided as a reusable adaptor. In some embodiments, the inventive adaptor can be both single-use and reusable in that the end-user will have the option to dispose of the adaptor after a single use or sterilize the adaptor and reuse it. This is achievable in particular because of the ability to form the adaptor from a variety of materials using a variety of methods. Thus, the adaptor can be sufficiently economical to justify making only a single use to avoid the need to sterilize. At the same time, the adaptor can be sufficiently sturdy to withstand multiple sterilization procedures.

As previously pointed out, the adaptor can be formed from a variety of different materials (including just the main body itself or including the main body and the gas inlet port). In some embodiments, the adaptor comprises a metal material. Preferably, the metal is non-corrosive (e.g., stainless steel or aluminum). In other embodiments, the adaptor comprises a polymeric material, which preferably is chemical resistant, heat resistant, or both chemical resistant and heat resistant. The use of medical grade plastic materials is particularly desirable. In one specific embodiment, the polymeric material is a polysulfone (e.g., polyphenylsulfone) or a similar material. Non-limiting examples of further polymeric materials that may be used to form one or more component of the inventive adaptor include polyethylene (e.g., UHME-PE), polypropylene, polymethylmethacrylate (PMMA), acetal copolymers, polythermide, polycarbonate, and polyetheretherketone (PEEK).

The adaptor of the invention may be provided as a stand-alone device. As such, the adaptor may be used with any water bottle that is sized appropriately to affix to the lower body portion of the adaptor, such as by screwing on via the supplied threads. Likewise, the adaptor may be used with any water bottle cap that is sized appropriately to affix to the upper body portion of the adaptor, such as by screwing on via the supplied threads. As noted above, it is not necessary for the water bottle cap that is to be sized appropriately to affix to the water bottle that is used since the adaptor may be a step-up convertor or a step-down convertor. Thus, it is possible to mix and match bottles and caps of different dimensions according to certain embodiments of the invention.

The adaptor also may be provided as part of a water bottle system, which may be a before market system (i.e., all components packaged and sold as a system) or an after market system (i.e., the components gathered by an end user and formed into the system). Thus, in certain embodiments, the invention also comprises a water bottle assembly or system for use with an endoscope.

In some embodiments, an assembly according to the invention may comprise the following components: 1) a water bottle having a neck portion with threads on the exterior surface thereof to facilitate attachment of another component; 2) a water bottle cap having walls and threads formed on the interior surface of the walls to facilitate attachment to another component; and 3) an adaptor according to any of the embodiments described herein. For example, in one embodiment, the adaptor used with the water bottle assembly may comprise a substantially tubular body having an interior surface and an exterior surface and having an upper portion and a lower portion, and may also comprise a gas inlet port extending outward from the exterior surface of the body and having a central passage extending through the body and opening on the interior surface of the body. More particularly, the upper body portion can have threads on the exterior surface and be removably affixed to the water bottle cap via the threads on each component. Further, the lower body portion can have threads on the interior surface and be removably affixed to the neck portion of the water bottle via the threads on each component. In certain embodiments, the assembly also may comprise one or more tubes affixed to one or more openings formed in the cap, the tubes functioning to transport fluid (e.g., liquid and/or gas) from the water bottle assembly to an endoscope. Preferably, at least one tube extends through the cap, through an interior passage in the adaptor, and into the bottle.

In other aspects, the present invention also provides various methods that make use of the inventive adaptor. For example, the invention can be directed to methods of performing an endoscopic procedure. In one embodiment, the method can comprise using an endoscope assembly that includes a water bottle with a cap and that also includes an adaptor according to any of the embodiments described herein. In other words, the inventive adaptor could be combined at the point of use with any variety of water bottles and bottle caps to perform an endoscopic procedure. The adaptor combined with the water bottle and bottle cap could then be used with any suitable endoscopy device such as, but not limited to, the systems described previously herein.

Such methods also could be carried out using a preformed water bottle assembly, such as described above. Particularly, an adaptor according to the invention could be provided at the point of use assembled or disassembled, packaged or unpackaged, with a water bottle and a bottle cap as a water bottle assembly that includes the bottle, the cap, and the adaptor.

As previously noted, the present invention is particularly beneficial in that it allows for the easy and efficient delivery of a secondary gas. Thus, in other aspects, the present invention also can be directed to methods for supplying a secondary gas in an endoscopic procedure. In certain embodiments, the method can comprise using an endoscopy assembly having attached thereto a water bottle with a cap. Particularly, the bottle may have a neck portion with threads on the external surface thereof, and the cap can have walls with threads formed on the interior surface thereof the method further can comprise using with the water bottle and cap an adaptor according to any embodiment of the present invention. In particular, the method can comprise affixing the inventive adaptor between the water bottle and the cap and supplying a secondary gas to the endoscopy assembly via the gas inlet port on the adaptor. Although any gas suitable for use in medical or veterinary procedures could be supplied, in particular embodiments, the secondary gas can comprise carbon dioxide.

As can be seen in FIG. 7, for example, in practice, the use of the inventive adaptor effectively moves the water bottle cap some distance away from the top of the water bottle. That distance effectively can be approximately the height of the upper portion of the main body of the adaptor. A standard water bottle cap having a water intake tube already affixed thereto may have a tube of defined length that substantially corresponds to the height of a standard water bottle. The added distance between the water bottle and the cap thus can effectively move the tube up in the bottle (i.e., a distance away from the bottle bottom that is substantially similar to the distance the adaptor moves the cap away from the top of the bottle). Accordingly, in some embodiments, it may be useful to include instructions with the adaptor that the water bottle may be filled with a somewhat greater than normal volume of water to accommodate for the raised tube. In other embodiments, the adaptor may comprise a tube extension that can be easily affixed to the end of a standard tube present in a water bottle cap to effectively lengthen the tube. The length of the tube extension can be substantially similar to the distance the adaptor moves the cap away from the top of the bottle (allowing for any overlap length where the tube extension is connected to the bottle cap tube).

In some embodiments, it may be preferred to minimize the height of the upper body portion of the adaptor to limit the above-described effect. In specific embodiments, the height of the upper body portion may be substantially identical to the height of the walls of a standard water bottle cap (i.e., a height sufficient to provide sufficient threading to attach the water bottle cap).

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An adaptor for an endoscopic water bottle, the adaptor comprising:
   a substantially tubular body having an interior surface and an exterior surface and having an upper body portion and a flared lower body portion, wherein the substantially tubular body is a one-piece structure;
   the upper body portion having threads on the exterior surface thereof suitable for attachment to threads on a water bottle cap;
   the flared lower body portion having threads on the interior surface thereof suitable for attachment to threads on a neck portion of the water bottle;
   and comprising a gas inlet port extending outward from the exterior surface of the body and having a central passage extending through the body and opening on the interior surface of the body,
   wherein the threads of the upper body portion are engageable with a thread configuration that is substantially identical to the threads of the flared lower body portion,
   wherein the upper body portion includes a groove on the exterior surface, and
   wherein the adaptor further comprises a sealing member associated with the exterior surface of the upper body portion, in which the sealing member is seated in the groove for forming a fluid tight seal between the adaptor and the water bottle cap.

2. The adaptor of claim 1, wherein the threads of the lower body portion are disposed on a first side of the threads of the upper body portion, and wherein the groove is formed on a second side of the threads of the upper body portion that is opposite the first side of the upper body portion.

3. The adaptor of claim 1, further comprising a sealing member associated with the interior surface of the flared lower body portion for forming a fluid tight seal between the adaptor and the water bottle.

4. The adaptor of claim 1, further comprising a substantially horizontal ledge on the interior surface of the body that delineates the interior surface of the upper body portion from the interior surface of the lower body portion.

5. The adaptor of claim 1, wherein an interior diameter of the upper body portion is less than an interior diameter of the lower body portion.

6. The adaptor of claim 1, wherein the adaptor further comprises a component for closing the gas inlet port to fluid passage.

7. The adaptor of claim 1, wherein the gas inlet port comprises a luer connector.

8. The adaptor of claim 1, wherein the adaptor body and gas inlet port are a one-piece structure.

9. The adaptor of claim 1, wherein the adaptor provides an open interior passage between a water bottle affixed to the lower body portion and a water bottle cap affixed to the upper body portion.

10. The adaptor of claim 1, wherein the gas inlet port is positioned such that an opening on the interior surface of the body is located between the threads on the upper body portion and the threads on the lower body portion.

11. The adaptor of claim 1, wherein the adaptor is a machined part or a molded part.

12. The adaptor of claim 1, wherein the adaptor is single-use or reusable.

13. The adaptor of claim 1, wherein the adaptor body comprises a metal material.

14. The adaptor of claim 1, wherein the adaptor is a step-up or step-down convertor.

\* \* \* \* \*